United States Patent
Harutyunyan et al.

(10) Patent No.: US 8,518,711 B2
(45) Date of Patent: Aug. 27, 2013

(54) QUANTITATIVE CHARACTERIZATION OF METALLIC AND SEMICONDUCTOR SINGLE-WALLED CARBON NANOTUBE RATIOS

(75) Inventors: Avetik R. Harutyunyan, Columbus, OH (US); Oleg Kuznetsov, Columbus, OH (US)

(73) Assignee: Honda Motor Co., Ltd., Tokyo (JP)

( * ) Notice: Subject to any disclaimer, the term of this patent is extended or adjusted under 35 U.S.C. 154(b) by 258 days.

(21) Appl. No.: 12/846,599

(22) Filed: Jul. 29, 2010

(65) Prior Publication Data
US 2013/0180018 A1    Jul. 11, 2013

(51) Int. Cl.
*G01N 21/76* (2006.01)
*G01N 21/00* (2006.01)
*G01N 33/00* (2006.01)

(52) U.S. Cl.
USPC .................. 436/172; 436/145; 436/164

(58) Field of Classification Search
None
See application file for complete search history.

(56) References Cited

U.S. PATENT DOCUMENTS

| | | | |
|---|---|---|---|
| 5,424,054 | A | 6/1995 | Bethune et al. |
| 6,974,492 | B2 | 12/2005 | Harutyunyan |
| 7,074,310 | B2 | 7/2006 | Smalley et al. |
| 7,264,876 | B2 | 9/2007 | Smalley et al. |

OTHER PUBLICATIONS

Arepalli, S. et al., "A Parametric Study of Single-Wall Carbon Nanotube Growth by Laser Ablation," *Journal of Nanoscience and Nanotechnology*, Sep. 2004, pp. 762-773, vol. 4, No. 7.
Arepalli, S. et al., "Diagnostics of Laser-produced Plume under Carbon Nanotube Growth Conditions," *Applied Physics A Materials Science & Processing*, 2000, pp. 125-133, vol. 70.
Arepalli, S., "Laser Ablation Process for Single-Walled Carbon Nanotube Production," *Journal of Nanoscience and Nanotechnology*, 2004, pp. 317-325, vol. 4, No. 4.
Arepalli, S. et al., "Spectral Measurements in Production of Single Wall Carbon Nanotubes by Laser Ablation," *Chemical Physics Letters*, Mar. 12, 1999, pp. 139-145, vol. 302.
Bachilo, S. et al., "Narrow (n,m)-Distribution of Single-Walled Carbon Nanotubes Grown Using a Solid Supported Catalyst," *J. Am. Chem. Soc.*, 2003, pp. 11186-11187, vol. 125.
Bachilo, S.M. et al., "Structure-Assigned Optical Spectra of Single-Walled Carbon Nanotubes," *Science*, Dec. 20, 2002, pp. 2361-2366, vol. 298.
Bethune, D.S. et al., "Cobalt-catalysed Growth of Carbon Nanotubes with Single-atomic-layer Walls," *Nature*, Jun. 17, 1993, vol. 363, pp. 605-607.
Blackburn, J. et al., "Transparent Conductive Single-Walled Carbon Nanotube Networks with Precisely Tunable Ratios of Semiconducting and Metallic Nanotubes," *ACS Nano*, 2008, pp. 1266-1274, vol. 2.
Chen, Z. et al., "Bulk Separative Enrichment in Metallic or Semiconducting Single-Walled Carbon Nanotubes," *Nano Lett.*, 2003, pp. 1245-1249, vol. 3, No. 9.

(Continued)

*Primary Examiner* — Yelena G Gakh
(74) *Attorney, Agent, or Firm* — Fenwick & West LLP; Mark E. Duell

(57) ABSTRACT

Methods and processes for quantitatively determining the ratio of the metallic to semiconductor tubes in the sample single-wall carbon nanotubes is provided. The single-walled carbon nanotubes can be sonicated to debundle the bulk material. The debundled SWNTs can be coated with a polymer, such as sulfonated polystyrene-block-poly(ethylene-ran-butylene)-block-polystyrene (SDPS), and the coated SWNTs can be deposited on a substrate. The total number of tubes can be determined by atomic force microscopy (AFM). The semiconducting nanotubes can be determined by photoluminescence spectroscopy. The combination of photoluminescence and AFM measurements provides a quantitative ratio of the metallic to semiconductor tubes in the sample.

14 Claims, 6 Drawing Sheets

(56) References Cited

OTHER PUBLICATIONS

Gao, M. et al., "Structure Determination of Individual Single-wall Nanotubes by Nanoarea Electron Diffraction," *Applied Physics Letters*, Apr. 21, 2003, pp. 2703-2705, vol. 82, No. 16.

Gomez-Gualdron, D. et al., "The Role of Cap Chirality in the Mechanism of Growth of Single-Wall Carbon Nanotubes," *Nanotechnology*, 2008, p. 485604 (1-7), vol. 19, No. 48.

Green, A., et al., "Colored Semitransparent Conductive Coatings Consisting of Monodiserse Metallic Single-Walled Carbon Nanotubes," *Nano Letters*, 2008, pp. 1417-1422, vol. 8, No. 5.

Harutyunyan, A. et al., "CVD Synthesis of Single Wall Carbon Nanotubes under 'Soft' Conditions," *Nano Letters*, 2002, pp. 525-530, vol. 2.

Iijima, S. et al., "Single-shell Carbon Nanotubes of 1-nm Diameter," *Nature*, Jun. 17, 1993, vol. 363, pp. 603-605.

Ivanov, V. et al., "The Study of Carbon Nanotubules Produced by Catalytic Method," *Chemical Physics Letters*, Jun. 24, 1994, pp. 329-335, vol. 223.

Jorio, A. et al., "Structural (n,m) Determination of Isolated Single-Wall Carbon Nanotubes by Resonant Raman Scattering," *Phys. Rev. Lett.*, 2001, pp. 1118-1121, vol. 86, No. 6.

Journet, C. et al., "Large-scale Production of Single-walled Carbon Nanotubes by the Electric-arc Technique," *Nature*, Aug. 21, 1997, pp. 756-758, vol. 388.

Kataura, H. et al., "Optical Properties of Single-Wall Carbon Nanotubes," *Synthetic Metals*, 1999, pp. 2555-2558, vol. 103.

Kim, W-J. et al., "Connecting Single Molecule Electrical Measurements to Ensemble Spectroscopic Properties for Quantification of Single-Walled Carbon Nanotube Separation," *J. Am. Chem. Soc.*, 2009, pp. 3128-3129, vol. 9.

Krupke, R. et al., "Separation of Metallic from Semiconducting Single-Walled Carbon Nanotubes," *Science*, Jul. 18, 2003, pp. 344-347, vol. 301.

Li, W. Z. et al., "Large-Scale Synthesis of Aligned Carbon Nanotubes," *Science*, Dec. 6, 1996, pp. 1701-1703, vol. 274.

Li, Y. et al., "Preferential Growth of Semiconducting Single-Walled Carbon Nanotubes by a Plasma Enhanced CVD Method," *Nano Lett.*, 2004, pp. 317-321, vol. 4, No. 2.

Lolli, G. et al., "Tailoring (n,m) Structure of Single-Walled Carbon Nanotubes by Modifying Reaction Conditions and the Nature of the Support of CoMo Catalysts," *J. Phys. Chem. B*, 2006, pp. 2108-2115, vol. 110, No. 5.

Lu, W. et al., "A Scanning Probe Microscopy Based Assay for Single-Walled Carbon Nanotube Metallicity," *Nano Lett.*, 2009, pp. 1668-1672, vol. 9, No. 4.

Miyata, Y. et al., "Optical Evaluation of the Metal-to-Semiconductor Ratio of Single-Wall Carbon Nanotubes," *J. Phys. Chem. C*, 2008, pp. 13187-13191, vol. 112.

Naumov, A. et al., "Quantifying the Semiconducting Fraction in Single-Walled Carbon Nanotube Samples throught Comparative Atomic Force and Photoluminescence Microscopies," *Nano Letters*, 2009, pp. 3203-3208, vol. 9, No. 9.

Nikolaev, P. et al., "Effect of Vaporization Temperature on the Diameter and Chiral Angle Distributions of Single-Walled Carbon Nanotubes," *J. Nanosci. Nanotech.*, 2010, pp. 3780-3789, vol. 10, No. 6.

O'Connell, M. et al., "Band Gap Fluorescence from Individual Single-Walled Carbon Nanotubes," *Science*, Jul. 26, 2002, pp. 593-596, vol. 297.

Qin, S. et al. "Helicity and Packing of Single-Walled Carbon Nanotubes Studied by Electron Nanodiffraction," *Chemical Physics Letters*, 1997, pp. 101-106, vol. 268.

Rao, A.M. et al., "Diameter-Selective Raman Scattering From Vibrational Modes in Carbon Nanotubes," *Science*, 1997, pp. 187-191, vol. 275.

Strano, M.S. et al., "Electronic Structure Control of Single-Walled Carbon Nanotube Functionalization," *Science*, 2003, pp. 1519-1522, vol. 301.

Thess, A. et al., "Crystalline Ropes of Metallic Carbon Nanotubes," *Science*, Jul. 26, 1996, pp. 483-487, vol. 273.

Tsyboulski, D.A., "Versatile Visualization of Individual Single-Walled Carbon Nanotubes with Near-Infrared Fluorescence Microscopy," *Nano Letters*, 2005, pp. 975-979, vol. 5, No. 5.

Vijayaraghavan, A. et al., "Imaging Electronic Structure of Carbon Nanotubes by Voltage-Contrast Scanning Electron Microscopy," *Nano Res*, 2008, pp. 321-332, vol. 1.

Weisman, R.B. et al., "Dependence of Optical Transition Energies on Structure for Single-Walled Carbon Nanotubes in Aqueous Suspension: An Empirical Kataura Plot," *Nano Letters*, 2003, pp. 1235-1238, vol. 3, No. 9.

Wildoer, J. et al., "Electronic Structure of Atomically Resolved Carbon Nanotubes," *Nature*, Jan. 1, 1998, pp. 59-62, vol. 391.

Zheng, M. et al., "Structure-based Carbon Nanotube Sorting by Sequence-Dependent DNA Assembly," *Science*, 2003, pp. 1545-1548, vol. 302.

QUANTITATIVE CHARACTERIZATION OF METALLIC AND SEMICONDUCTOR SINGLE-WALLED CARBON NANOTUBE RATIOS

FIELD

The present disclosure relates to methods for the preparation (synthesis) of carbon single-walled nanotubes and methods for characterization of the metallic and semiconductor single-walled nanotubes formed.

BACKGROUND

Carbon nanotubes are hexagonal networks of carbon atoms forming seamless tubes with each end capped with half of a fullerene molecule. They were first reported in 1991 by Sumio Iijima who produced multi-layer concentric tubes or multi-walled carbon nanotubes by evaporating carbon in an arc discharge. They reported carbon nanotubes having up to seven walls. In 1993, Iijima's group and an IBM team headed by Donald Bethune independently discovered that a single-wall nanotube could be made by vaporizing carbon together with a transition metal such as iron or cobalt in an arc generator (see Iijima et al. Nature 363:603 (1993); Bethune et al., Nature 363: 605 (1993) and U.S. Pat. No. 5,424,054). The original syntheses produced low yields of non-uniform nanotubes mixed with large amounts of soot and metal particles.

Presently, there are three main approaches for the synthesis of single- and multi-walled carbon nanotubes. These include the electric arc discharge of graphite rod (Journet et al. Nature 388: 756 (1997)), the laser ablation of carbon (Thess et al. Science 273: 483 (1996)), and the chemical vapor deposition of hydrocarbons (Ivanov et al. Chem. Phys. Lett 223: 329 (1994); Li et al. Science 274: 1701 (1996)). Multi-walled carbon nanotubes can be produced on a commercial scale by catalytic hydrocarbon cracking while single-walled carbon nanotubes are still produced on a gram scale.

Generally, single-walled carbon nanotubes are preferred over multi-walled carbon nanotubes because they have unique mechanical and electronic properties. Defects are less likely to occur in single-walled carbon nanotubes because multi-walled carbon nanotubes can survive occasional defects by forming bridges between unsaturated carbon valances, while single-walled carbon nanotubes have no neighboring walls to compensate for defects. Defect-free single-walled nanotubes are expected to have remarkable mechanical, electronic and magnetic properties that could be tunable by varying the diameter, number of concentric shells, and chirality of the tube. Nanotubes can have various crystal orientations and diameters which produces a variety of electronic band structures. Thus, SWNTs can either metallic or semiconducting depending on its chirality. Metallic nanotubes can carry extremely large current densities with constant resistivity. Semiconducting nanotubes can be electrically switched on and off as field-effect transistors (FETs).

It is generally recognized that an estimation of the ratio of the metallic to semiconductor tubes in a sample is important for the use of the nanotubes. However, at present, a reliable method for obtaining the ratio of metallic to semiconductor tubes is not available. U.S. Pat. No. 7,264,876, entitled "Polymer-wrapped single wall carbon nanotubes," to Rice University describes single-wall carbon nanotube partially coated with polymer for use in antennas, electromagnetic and electro-optic devices. The reference discloses suspending the nanotubes in a solvent by associating them with linear polymers that are soluble in the solvent. The solvent is said to be water, and the polymers used include polyvinyl pyrrolidone and polystyrene sulfonate. U.S. Pat. No. 7,074,310, entitled "Method for separating single-walled carbon nanotubes and compositions thereof" to Rice University describes the separation of (n,m) type of SWNTs. The method involves suspending the nanotubes in liquid to form a suspension, acidifying the suspension to protonate the nanotubes, and applying an electric field where the protonated nanotubes migrate in the electric fields at different rates depending on their metallic nature.

Reliable characterization is important to the preparation of pure semiconducting or metallic SWNT samples. At the level of individual nanotubes, the two types can be distinguished and counted by specific (n,m) determination through highly resolved scanning tunneling microscopy (STM) (Wildoer et al., Nature, 391:59-62 (1998)) or electron nanodiffraction (Qin et al., Chem Phys Lett, 268:101-106 (1997); Gao et al., Appl Phys Lett, 82:2703-2705 (2003)). However, these precise microscopic methods are too tedious for routine use. The metallic/semiconducting composition of a sample can also in principle be determined by counting individual nanotubes using voltage-contrast SEM, which distinguishes metallic from semiconducting SWNTs (Vijayaraghavan et al., Nano Res, 1:321-332 (2009)). This approach involves the complexity of size exclusion chromatography followed by electrophoretic SWNT deposition. In addition, systematic errors may arise from nonuniform sampling or the presence of small bundles of mixed electronic type. Recently, electric force scanning probe microscopy has been applied to recognize and count individual metallic and semiconducting SWNTs longer than 200 nm and determine sample compositions (Lu et al., Nano Lett, 9:1668-1672 (2009)). Another counting-based method is direct charge transport or electrical breakdown measurements on SWNT field-effect transistors to classify nanotubes as metallic or semiconducting (Kim et al., J Am Chem Soc, 131:3128-3129 (2009); Li et al., Nano Lett, 4:317-321 (2004)). The laborious nature of this approach makes it difficult to achieve high statistical accuracy, and results may also be influenced by clustering and sampling inefficiency.

Despite the interest in the field for a method of determining the ratio of metallic to semiconducting carbon single-walled nanotubes (SWNTs) in samples, no reliable and usable method has yet been identified. Therefore, there is a need in the field for improved methods and processes for estimating the ratio of the metallic to semiconductor carbon single-walled nanotubes (SWNTs) in a sample.

SUMMARY

The present disclosure addresses these long-felt needs in the field by providing novel methods and processes for quantitatively determining the ratio of metallic to semiconductor single-wall carbon nanotubes in a sample.

In certain aspects, the present disclosure provides a method for quantitatively determining the ratio of metallic and semiconductor single-wall carbon nanotubes (SWNT) in a sample, the method comprising debundling the SWNTs to provide substantially individual SWNTs; measuring an atomic force microscopy (AFM) signal in a sample, wherein the AFM signal is produced by SWNTs, and wherein SWNTs comprise a mixture of semiconductor and metallic SWNTs; measuring a photoluminescence (PL) signal in a sample, wherein the PL signal is produced by semiconductor SWNTs; and determining the ratio of metallic and semiconductor SWNTs in the sample by comparing the signals corresponding to total SWNTs and the semiconducting SWNTs, wherein the ratio of metallic and semiconductor SWNTs is quantitatively determined.

In certain aspects, the SWNTs are coated with sulfonated polystyrene-block-poly(ethylene-ran-butylene)-block-polystyrene (SDPS) via spin coating and deposited on a substrate.

These and other aspects of the present invention will become evident upon reference to the following detailed description. In addition, various references are set forth herein which describe in more detail certain procedures or compositions, and are therefore incorporated by reference in their entirety.

DETAILED DESCRIPTION

Figure 1:
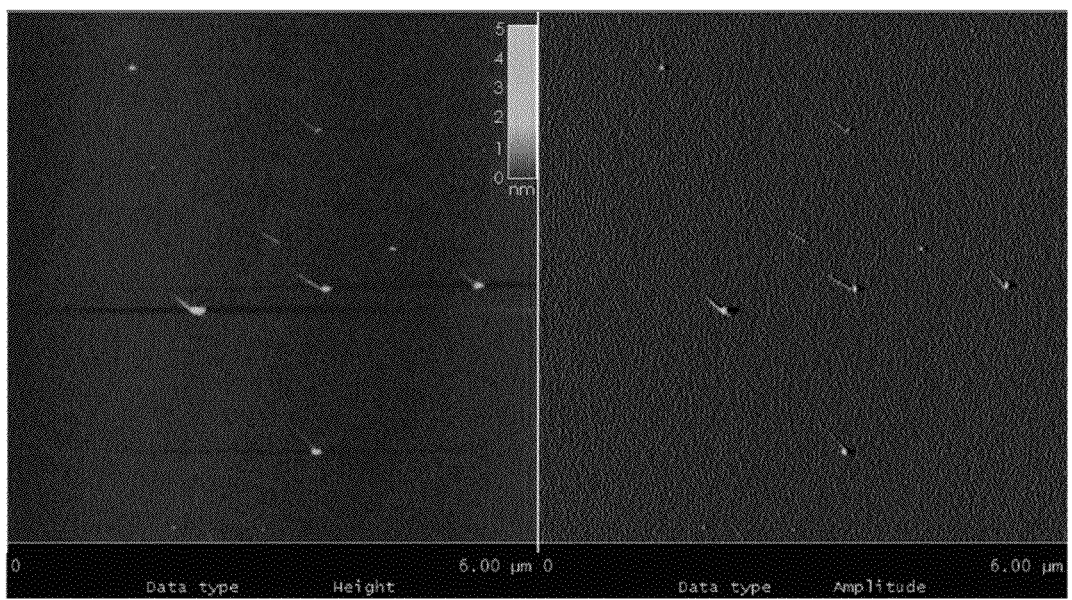
FIG. 1 depicts atomic force microscopy (AFM) images of individual single-walled carbon nanotubes (SWNTs). Tapping mode AFM images of individual SWNTs were produced from a density gradient ultracentrifugation (DGU) processed semiconducting enriched sample in dried SDS on a cleaved mica surface. The amplitude image is shown in the right panel; height is shown in the left panel. Each panel shows a 6×6 μm region.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise.

The terms "single-walled carbon nanotube" or "one-dimensional carbon nanotube" are used interchangeable and refer to cylindrically shaped thin sheet of carbon atoms having a wall consisting essentially of a single layer of carbon atoms, and arranged in a hexagonal crystalline structure with a graphitic type of bonding.

The term "multi-walled carbon nanotube" as used herein refers to a nanotube composed of more than one concentric tubes.

I. Overview

The present disclosure provides for methods, apparatuses, and processes for quantitatively determining the ratio of metallic to semiconductor single-wall carbon nanotubes in a sample.

The present disclosure relates to methods and processes for quantitating carbon nanotubes by chirality type based upon their electronic and optical properties. The single-walled carbon nanotubes can be sonicated to debundle the bulk material. The debundled SWNTs can be coated with a polymer, such as sulfonated polystyrene-block-poly(ethylene-ran-butylene)-block-polystyrene (SDPS), and the coated SWNTs can be deposited on a substrate. The total number of tubes can be determined by atomic force microscopy (AFM). The semiconducting nanotubes can be determined by photoluminescence. The total numbers of metallic and semiconducting nanotubes can then be compared to provide a ratio of metallic and semiconducting SWNTs. Thus, the combination of photoluminescence spectroscopy and AFM provides a quantitative ratio of the metallic to semiconductor tubes in the sample.

II. The Catalyst

The catalyst composition may be any catalyst composition known to those of skill in the art that is routinely used in chemical vapor deposition processes. The function of the catalyst in the carbon nanotube growth process is to decompose the carbon precursors and aid the deposition of ordered carbon. The method, processes, and apparatuses of the present invention preferably use metal nanoparticles as the metallic catalyst. The metal or combination of metals selected as the catalyst can be processed to obtain the desired particle size and diameter distribution. The metal nanoparticles can then be separated by being supported on a material suitable for use as a support during synthesis of carbon nanotubes using the metal growth catalysts described below. As is known in the art, the support can be used to separate the catalyst particles from each other thereby providing the catalyst materials with greater surface area in the catalyst composition. Such support materials include powders of crystalline silicon, polysilicon, silicon nitride, tungsten, magnesium, aluminum and their oxides, preferably aluminum oxide, silicon oxide, magnesium oxide, or titanium dioxide, or combination thereof, optionally modified by addition elements, are used as support powders. Silica, alumina and other materials known in the art may be used as supports, preferably alumina is used as the support.

The metal catalyst can be selected from a Group V metal, such as V or Nb, and mixtures thereof, a Group VI metal including Cr, W, or Mo, and mixtures thereof, VII metal, such as, Mn, or Re, Group VIII metal including Co, Ni, Ru, Rh, Pd, Os, Ir, Pt, and mixtures thereof, or the lanthanides, such as Ce, Eu, Er, or Yb and mixtures thereof, or transition metals such as Cu, Ag, Au, Zn, Cd, Sc, Y, or La and mixtures thereof. Specific examples of mixture of catalysts, such as bimetallic catalysts, which may be employed by the present invention include Co—Cr, Co—W, Co—Mo, Ni—Cr, Ni—W, Ni—Mo, Ru—Cr, Ru—W, Ru—Mo, Rh—Cr, Rh—W, Rh—Mo, Pd—Cr, Pd—W, Pd—Mo, Ir—Cr, Pt—Cr, Pt—W, and Pt—Mo. Preferably, the metal catalyst is iron, cobalt, nickel, molybdenum, or a mixture thereof, such as Fe—Mo, Co—Mo and Ni—Fe—Mo.

The metal, bimetal, or combination of metals are used to prepare metal nanoparticles having defined particle size and diameter distribution. The metal nanoparticles can be prepared using the literature procedure described in described in Harutyunyan et al., NanoLetters 2, 525 (2002). Alternatively, the catalyst nanoparticles can be prepared by thermal decomposition of the corresponding metal salt added to a passivating salt, and the temperature of the solvent adjusted to provide the metal nanoparticles, as described in the co-pending and co-owned U.S. patent application Ser. No. 10/304,316, or by any other method known in the art. The particle size and diameter of the metal nanoparticles can be controlled by using the appropriate concentration of metal in the passivating solvent and by controlling the length of time the reaction is allowed to proceed at the thermal decomposition temperature. Metal nanoparticles having particle size of about 0.01 nm to about 20 nm, more preferably about 0.1 nm to about 3 nm and most preferably about 0.3 nm to 2 nm can be prepared. The metal nanoparticles can thus have a particle size of 0.1, 1, 2, 3, 4, 5, 6, 7, 8, 9, or 10 nm, and up to about 20 nm. In another aspect, the metal nanoparticles can have a range of particle sizes. For example, the metal nanoparticles can have particle sizes in the range of about 3 nm and about 7 nm in size, about 5 nm and about 10 nm in size, or about 8 nm and about 16 nm in size. The metal nanoparticles can optionally have a diameter distribution of about 0.5 nm to about 20 nm, preferably about 1 nm to about 15 nm, more preferably about 1 nm to about 5 nm. Thus, the metal nanoparticles can have a diameter distribution of about 1, 2, 3, 4, 5, 6, 7, 8, 9, 10, 11, 12, 13, 14, or 15 nm.

The metal salt can be any salt of the metal, and can be selected such that the melting point of the metal salt is lower than the boiling point of the passivating solvent. Thus, the metal salt contains the metal ion and a counter ion, where the counter ion can be nitrate, nitride, perchlorate, sulfate, sulfide, acetate, halide, oxide, such as methoxide or ethoxide, acetylacetonate, and the like. For example, the metal salt can be iron acetate ($FeAc_2$), nickel acetate ($NiAc_2$), palladium acetate ($PdAc_2$), molybdenum acetate ($MoAc_3$), and the like, and combinations thereof. The melting point of the metal salt is preferably about 5° C. to 50° C. lower than the boiling point, more preferably about 5° C. to about 20° C. lower than the boiling point of the passivating solvent.

The metal salt can be dissolved in a passivating solvent to give a solution, a suspension, or a dispersion. The solvent is preferably an organic solvent, and can be one in which the chosen metal salt is relatively soluble and stable, and where the solvent has a high enough vapor pressure that it can be easily evaporated under experimental conditions. The solvent can be an ether, such as a glycol ether, 2-(2-butoxyethoxy) ethanol, $H(OCH_2CH_2)_2$—O—$(CH_2)_3CH_3$, which will be referred to below using the common name dietheylene glycol mono-n-butyl ether, and the like.

The relative amounts of metal salt and passivating solvent are factors in controlling the size of nanoparticles produced. A wide range of molar ratios, here referring to total moles of metal salt per mole of passivating solvent, can be used for forming the metal nanoparticles. Typical molar ratios of metal salt to passivating solvent include ratios as low as about 0.0222 (1:45), or as high as about 2.0 (2:1), or any ratio in between. Thus, for example, about $5.75 \times 10^{-5}$ to about $1.73 \times 10^{-3}$ moles (10-300 mg) of $FeAc_2$ can be dissolved in about $3 \times 10^{-4}$ to about $3 \times 10^{-3}$ moles (50-500 ml) of diethylene glycol mono-n-butyl ether.

In another aspect, more than one metal salt can be added to the reaction vessel in order to form metal nanoparticles composed of two or more metals, where the counter ion can be the same or can be different. The relative amounts of each metal salt used can be a factor in controlling the composition of the resulting metal nanoparticles. For the bimetals, the molar ratio of the first metal salt to the second metal salt can be about 1:10 to about 10:1, preferably about 2:1 to about 1:2, or more preferably about 1.5:1 to about 1:1.5, or any ratio in between. Thus, for example, the molar ratio of iron acetate to nickel acetate can be 1:2, 1:1.5, 1.5:1, or 1:1. Those skilled in the art will recognize that other combinations of metal salts and other molar ratios of a first metal salt relative to a second metal salt may be used in order to synthesize metal nanoparticles with various compositions.

The passivating solvent and the metal salt reaction solution can be mixed to give a homogeneous solution, suspension, or dispersion. The reaction solution can be mixed using standard laboratory stirrers, mixtures, sonicators, and the like, optionally with heating. The homogenous mixture thus obtained can be subjected to thermal decomposition in order to form the metal nanoparticles.

The thermal decomposition reaction is started by heating the contents of the reaction vessel to a temperature above the melting point of at least one metal salt in the reaction vessel. Any suitable heat source may be used including standard laboratory heaters, such as a heating mantle, a hot plate, or a Bunsen burner, and the heating can be under reflux. The length of the thermal decomposition can be selected such that the desired size of the metal nanoparticles can be obtained. Typical reaction times can be from about 10 minutes to about 120 minutes, or any integer in between. The thermal decomposition reaction is stopped at the desired time by reducing the temperature of the contents of the reaction vessel to a temperature below the melting point of the metal salt.

The size and distribution of metal nanoparticles produced can be verified by any suitable method. One method of verification is transmission electron microscopy (TEM). A suitable model is the Phillips CM300 FEG TEM that is commercially available from FEI Company of Hillsboro, Oreg. In order to take TEM micrographs of the metal nanoparticles, one or more drops of the metal nanoparticle/passivating solvent solution are placed on a carbon membrane grid or other grid suitable for obtaining TEM micrographs. The TEM apparatus is then used to obtain micrographs of the nanoparticles that can be used to determine the distribution of nanoparticle sizes created.

The metal nanoparticles, such as those formed by thermal decomposition described in detail above, can then be supported on solid supports. The solid support can be silica, alumina, MCM-41, MgO, $ZrO_2$, aluminum-stabilized magnesium oxide, zeolites, or other oxidic supports known in the art, and combinations thereof. For example, $Al_2O_3$—$SiO_2$ hybrid support could be used. Preferably, the support is aluminum oxide ($Al_2O_3$) or silica ($SiO_2$). The oxide used as solid support can be powdered thereby providing small particle sizes and large surface areas. The powdered oxide can preferably have a particle size between about 0.01 ™ to about 100 µm, more preferably about 0.1 ™ to about 10 µm, even more preferably about 0.5 ™ to about 5 µm, and most preferably about 1 µm to about 2 µm. The powdered oxide can have a surface area of about 50 to about 1000 $m^2/g$, more preferably a surface area of about 200 to about 800 $m^2/g$. The powdered oxide can be freshly prepared or commercially available.

In one aspect, the metal nanoparticles are supported on solid supports via secondary dispersion and extraction. Secondary dispersion begins by introducing particles of a powdered oxide, such as aluminum oxide ($Al_2O_3$) or silica ($SiO_2$), into the reaction vessel after the thermal decomposition reaction. A suitable $Al_2O_3$ powder with 1-2 µm particle size and having a surface area of 300-500 $m^2/g$ is commercially available from Alfa Aesar of Ward Hill, Mass., or Degussa, N.J. Powdered oxide can be added to achieve a desired weight ratio between the powdered oxide and the initial amount of metal used to form the metal nanoparticles. Typically, the weight ratio can be between about 10:1 and about 15:1. For example, if 100 mg of iron acetate is used as the starting material, then about 320 to 480 mg of powdered oxide can be introduced into the solution.

The mixture of powdered oxide and the metal nanoparticle/passivating solvent mixture can be mixed to form a homogenous solution, suspension or dispersion. The homogenous solution, suspension or dispersion can be formed using sonicator, a standard laboratory stirrer, a mechanical mixer, or any other suitable method, optionally with heating. For example, the mixture of metal nanoparticles, powdered oxide, and passivating solvent can be first sonicated at roughly 80° C. for 2 hours, and then sonicated and mixed with a laboratory stirrer at 80° C. for 30 minutes to provide a homogenous solution.

After secondary dispersion, the dispersed metal nanoparticles and powdered oxide can be extracted from the passivating solvent. The extraction can be by filtration, centrifugation, removal of the solvents under reduced pressure, removal of the solvents under atmospheric pressure, and the like. For example, extraction includes heating the homogenized mixture to a temperature where the passivating solvent has a significant vapor pressure. This temperature can be maintained until the passivating solvent evaporates, leaving behind the metal nanoparticles deposited in the pores of the $Al_2O_3$. For example, if diethylene glycol mono-n-butyl ether as the passivating solvent, the homogenous dispersion can be heated to 231° C., the boiling point of the passivating solvent, under an $N_2$ flow. The temperature and $N_2$ flow are maintained until the passivating solvent is completely evaporated. After evaporating the passivating solvent, the powdered oxide and metal nanoparticles are left behind on the walls of the reaction vessel as a film or residue. When the powdered oxide is $Al_2O_3$, the film will typically be black. The metal nanoparticle and powdered oxide film can be removed from the reaction vessel and ground to create a fine powder, thereby increasing the available surface area of the mixture. The mixture can be ground with a mortar and pestle, by a commercially available mechanical grinder, or by any other methods of increasing the surface area of the mixture will be apparent to those of skill in the art.

As noted above, the weight ratio of metal nanoparticles to powdered oxide can be between about 1:10 and 1:15, such as, for example, 1:11, 1:12, 2:25, 3:37, 1:13, 1:14, and the like. The relatively larger amount of powdered oxide in effect serves to further separate or "dilute" the metal nanoparticles as the passivating solvent is removed. The process thus provides metal nanoparticles of defined particle size.

As will be apparent to those of skill in the art, the catalyst thus prepared can be stored for later use. In another aspect, the metal nanoparticles can be previously prepared, isolated from the passivating solvent, and purified, and then added to a powdered oxide in a suitable volume of the same or different passivating solvent. The metal nanoparticles and powdered oxide can be homogenously dispersed, extracted from the passivating solvent, and processed to increase the effective surface area as described above. Other methods for preparing the metal nanoparticle and powdered oxide mixture will be apparent to those skilled in the art.

The metal nanoparticles thus formed can be used as a growth catalyst for synthesis of carbon nanotubes, nanofibers, and other one-dimensional carbon nanostructures by a chemical vapor deposition (CVD) process.

III. Carbon Precursors

The carbon nanotubes can be synthesized using carbon precursors, such as carbon containing gases. In general, any carbon containing gas that does not pyrolize at temperatures up to 800° C. to 1000° C. can be used. Examples of suitable carbon-containing gases include carbon monoxide, aliphatic hydrocarbons, both saturated and unsaturated, such as methane, ethane, propane, butane, pentane, hexane, ethylene, acetylene and propylene; oxygenated hydrocarbons such as acetone, and methanol; aromatic hydrocarbons such as benzene, toluene, and naphthalene; and mixtures of the above, for example carbon monoxide and methane. In general, the use of acetylene promotes formation of multi-walled carbon nanotubes, while carbon monoxide and methane are preferred feed gases for formation of single-walled carbon nanotubes. The carbon-containing gas may optionally be mixed with a diluent gas such as hydrogen, helium, argon, neon, krypton and xenon or a mixture thereof IV. Synthesis of Carbon Nanotubes The methods and processes of the invention provide for the synthesis of SWNTs with a narrow distribution of diameters. The narrow distribution of carbon nanotube diameters is obtained by activating small diameter catalyst particles preferentially during synthesis by selecting the lowest eutectic point as the reaction temperature.

In one aspect of the invention, the metal nanoparticles supported on powdered oxides can be contacted with the carbon source at the reaction temperatures according to the literature methods described in Harutyunyan et al., NanoLetters 2, 525 (2002). Alternatively, the metal nanoparticles supported on the oxide powder can be aerosolized and introduced into the reactor maintained at the reaction temperature. Simultaneously, the carbon precursor gas is introduced into the reactor. The flow of reactants within the reactor can be controlled such that the deposition of the carbon products on the walls of the reactor is reduced. The carbon nanotubes thus produced can be collected and separated.

The metal nanoparticles supported on the oxide powder can be aerosolized by any of the art known methods. In one method, the supported metal nanoparticles are aerosolized using an inert gas, such as helium, neon, argon, krypton, xenon, or radon. Preferably argon is used. Typically, argon, or any other gas, is forced through a particle injector, and into the reactor. The particle injector can be any vessel that is capable of containing the supported metal nanoparticles and that has a means of agitating the supported metal nanoparticles. Thus, the catalyst deposited on a powdered porous oxide substrate can be placed in a beaker that has a mechanical stirrer attached to it. The supported metal nanoparticles can be stirred or mixed in order to assist the entrainment of the catalyst in the transporter gas, such as argon.

Thus, the nanotube synthesis generally occurs as described in the co-pending and co-owned application, U.S. Ser. No. 10/727,707, filed on Dec. 3, 2003. An inert transporter gas, preferably argon gas, is generally passed through a particle injector. The particle injector can be a beaker or other vessel containing the growth catalyst supported on a powdered porous oxide substrate. The powdered porous oxide substrate in the particle injector can be stirred or mixed in order to assist the entrainment of the powdered porous oxide substrate in the argon gas flow. Optionally, the inert gas can be passed through a drying system to dry the gas. The argon gas, with the entrained powdered porous oxide, can then be passed through a pre-heater to raise the temperature of this gas flow to about 400° C. to about 500° C. The entrained powdered porous oxide is then delivered to the reaction chamber. A flow of methane or another carbon source gas and hydrogen is also delivered to the reaction chamber. The typical flow rates can be 500 sccm for argon, 400 sccm for methane, and 100 sccm for He. Additionally, 500 sccm of argon can be directed into the helical flow inlets to reduce deposition of carbon products on the wall of the reaction chamber. The reaction chamber can be heated to between about 300° C. and 900° C. during the reaction using a suitable heater. The temperature is preferably kept below the decomposition temperature of the carbon precursor gas. For example, at temperatures above 1000° C., methane is known to break down directly into soot rather than forming carbon nanostructures with the metal growth catalyst. Carbon nanotubes and other carbon nanostructures synthesized in reaction chamber can then be collected and characterized.

The carbon nanotubes and nanostructures produced by the methods and processes described above can be used in applications that include Field Emission Devices, Memory devices (high-density memory arrays, memory logic switching arrays), Nano-MEMs, AFM imaging probes, distributed diagnostics sensors, and strain sensors. Other key applications include: thermal control materials, super strength and light weight reinforcement and nanocomposites, EMI shielding materials, catalytic support, gas storage materials, high surface area electrodes, and light weight conductor cable and wires, and the like.

V. Quantitative Characterization of SWNTs

The carbon SWNTs synthesized above are typically bundles and individual SWNTs. The bundled SWNTs can be treated to provide individual SWNTs by any one of the known methods. For example, the bulk product, containing the bundles and individual SWNTs, can be placed in a solvent and sonicated using commercially available sonicators. The sonication can be for about 30 seconds to about 3 hours, or until mostly individual SWNTs are produced. Atomic force microscopy (AFM) can be used to evaluate the debundling process to ensure that primarily individual SWNTs are present. FIG. 1 shows an AFM image of SWNTs and demonstrates that sonication results in mostly individual SWNTs.

In certain aspects, the present disclosure provides for a method for quantitatively determining the ratio of metallic and semiconductor single-wall carbon nanotubes (SWNT) in a sample, the method comprising debundling the SWNTs to provide substantially individual SWNTs; measuring an atomic force microscopy (AFM) signal in a sample, wherein the AFM signal is produced by SWNTs, and wherein SWNTs comprise a mixture of semiconductor and metallic SWNTs; measuring a photoluminescence (PL) signal in a sample, wherein the PL signal is produced by semiconductor SWNTs; and determining the ratio of metallic and semiconductor SWNTs in the sample by comparing the signals corresponding to total SWNTs and the semiconducting SWNTs, wherein the ratio of metallic and semiconductor SWNTs is quantitatively determined.

In one aspect of the present disclosure, the single-wall carbon nanotubes, can be coated with a polymer using spin coating techniques. The SWNTs can be coated with a polymer wherein the polymer is present as a mono-molecular layer on the SWNT, or where the polymer wraps or coats only part of the exterior surface of the SWNT. A variety of polymers can be used in the present invention. Thus, the polymer can be sulfonated polystyrene-block-poly(ethylene-ran-butylene)-block-polystyrene (SDPS), polyvinyl pyrrolidone (PVP), polystyrene sulfonate (PSS), poly(1-vinyl pyrrolidone-co-vinyl acetate) (PVP/VA), poly(1-vinyl pyrrolidone-coacrylic acid), poly(1-vinyl pyrrolidone-co-dimethylaminoethyl methacrylate), polyvinyl sulfate, poly(sodium styrene sulfonic acid-co-maleic acid), dextran sulfate, poly(methyl methacrylate-co-ethyl acrylate), polyvinyl alcohol, polyethylene glycol, and mixtures thereof. Preferably, the polymer is SDPS. Attachment to the SWNTs can be confirmed by use of optical and microscopic techniques, such as Raman, photoluminescence, near-field scanning microscopy, atomic force microscopy (AFM), and transmission electron microscopy (TEM).

The coated carbon nanotube can be prepared by known methods. For example, the carbon nanotube and/or the polymer can be dispersed in a solvent (either simultaneously or sequentially) and a salt to promote wrapping of polymer on the carbon nanotube can be added, whereby polymer becomes wrapped on the exterior of the carbon nanotubes.

After the SWNTs have been coated with polymer, it can be transferred to a smooth substrate for analysis. The substrate can be quartz, glass, plastic, and the like. The coated SWNTs can be transferred to the substrate by spin coating technique, for example.

Figure 3:
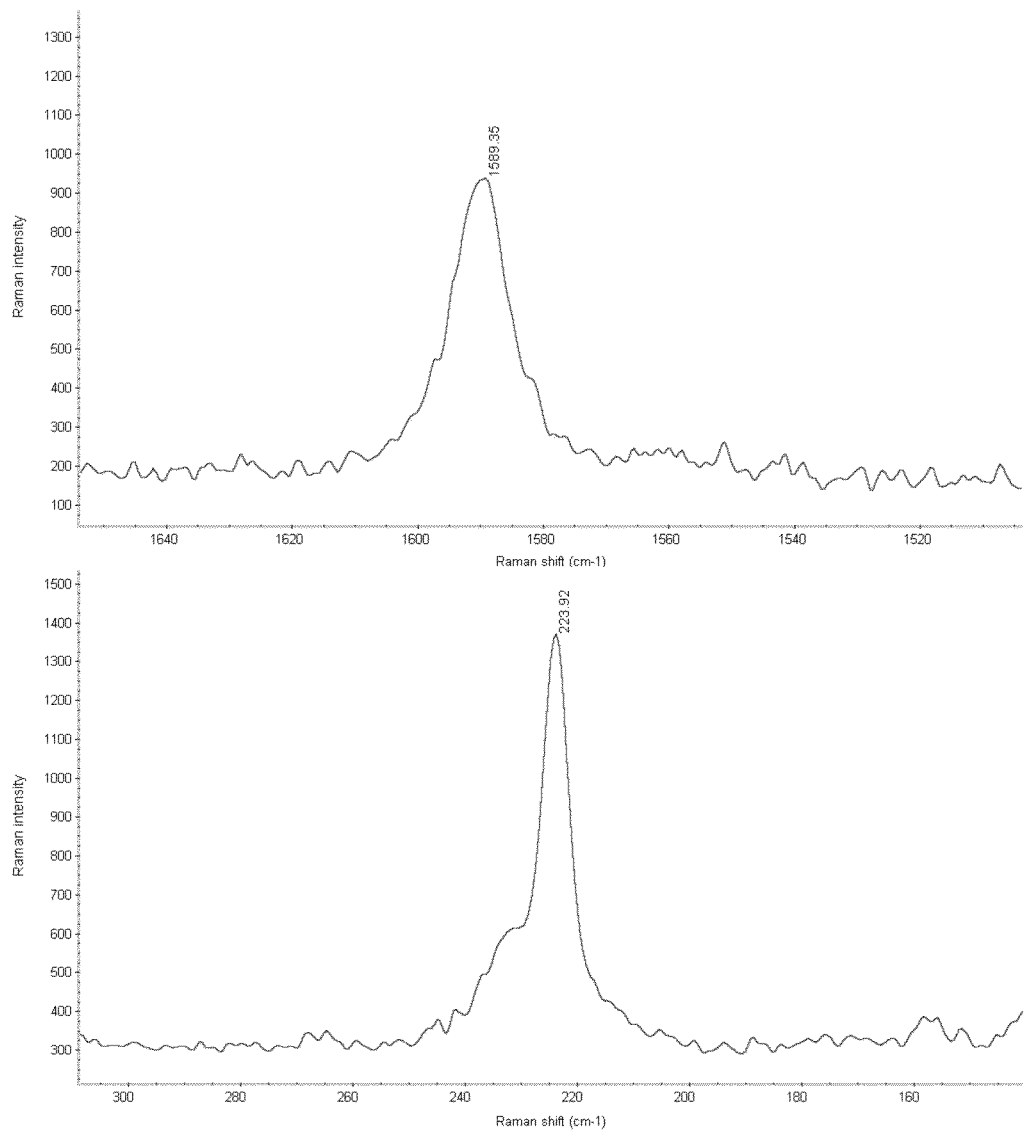
FIG. 3 depicts the Raman spectra of carbon SWNTs ($\lambda$=532 nm excitation). The top panel shows an example of the Raman G-band and the bottom panel shows the RBM spectra of individual SWNTs (laser excitation wavelength $\lambda$=785 nm).

The chirality distribution of the semiconducting carbon nanotubes, for example, as shown in FIG. 3, can be measured using Raman scattering testing and absorption testing, using multiple different laser excitations, such as, for example, λ=1064; 785; 614, 532, 514 and 488 nm.

Typically, the Raman spectra of SWNTs has three major peaks, which are the G-band at about 1590 cm$^{-1}$, D-band at about 1350 cm$^{-1}$, and the radial breathing mode (RBM) at about 100-300 cm$^{-1}$. RBM frequency is proportional to an inverse of the diameter of SWNTs and can thus be used to calculate the diameter of the SWNT. Normally, a red shift in RBM peak corresponds to an increase in the mean diameter of SWNTs. The tangential mode G-band related to the Raman-allowed phonon mode $E_{2g}$ can be a superposition of two peaks. The double peak at about 1593 and 1568 cm$^{-1}$ has been assigned to semiconductor SWNTs, while the broad Breit-Wigner-Fano line at about 1550 cm$^{-1}$ has been assigned to metallic SWNTs. Thus, the G-band offers a method for distinguishing between metallic and semiconducting SWNTs. The D-band structure is related to disordered carbon, the presence of amorphous carbon, and other defects due to the sp$^2$-carbon network. FIG. 3 shows peaks corresponding to metallic and semiconducting carbon nanotubes.

In contrast to metallic nanotubes, semiconducting nanotube types are able to absorb radiation and luminesce. Luminescence can be fluorescence, phosphorescence, photoluminescence, other forms of optical emission, thermoluminescence, electroluminescence and combinations thereof. For semiconducting nanotubes, the diameter and chirality of the nanotube determine the electronic band-gap and hence the wavelength at which the nanotube will absorb incident photons and exhibit photoluminescence. Luminescence of the polymer coated nanotubes, as described above, can be used to determine the amount of semiconducting nanotubes in the sample. Alternatively, the excitation and photoluminescence emission frequencies can be correlated with Raman shifts using variable laser frequencies to determine the correspondence for each particular (n,m) tube type.

Photoluminescence (PL) spectroscopy offers an incisive probe of bulk or individual semiconducting SWNTs (Bachilo et al., Science, 298:2361-2366 (2002); Weisman et al., Nano Lett, 3:1235-1238 (2003); Tsyboulski et al., Nano Lett, 5:975-979 (2005)), but does not detect metallic species. Raman spectroscopy also provides a relatively rapid tool for studying SWNTs as individuals or bulk ensembles (Jorio et al., Phys Rev Lett, 86:1118-1121 (2001); Rao et al., Science, 275:187-191 (1997)). However, it has the disadvantage of requiring a wide variety of incident laser wavelengths to detect nanotubes spanning a range of structures. Raman has been used to estimate the relative semiconducting and metallic contents in processed SWNT samples (Zheng et al., Science, 302:1545-1548 (2003); Strano et al., Science, 301:1519-1522 (2003); Krupke et al., Science, 301:344-347 (2003)), but the calibration factors needed to extract reliable values of these ratios are not known. Visible-near-IR absorption spectroscopy of SWNT samples reveals distinct optical transitions of semiconducting and metallic species (Chen et al., Nano Lett, 3:1245-1249 (2003); Kataura et al., Synth Met, 103:2555-2558 (1999)) and is thus more useful for quantitative determination of metallic/semiconducting ratios. While recent work has been conducted in this area Kim et al., J Am Chem Soc, 131:3128-3129 (2009); Miyata et al., J Phys Chem C, 112:13187-13191 (2008); Blackburn et al., ACS Nano, 2:1266-1274 (2008)), these researchers have failed to accurately subtract background absorptions and have been unable to acquire well-characterized reference samples.

The present disclosure provides for the absolute measurement of the semiconducting fractions in SWNT samples using novel counting-based methods. Using this approach, AFM and near-IR photoluminescence images of dried dilute SWNT dispersions are captured. Both semiconducting and metallic species are visible in the AFM images, while only semiconducting nanotubes are visible in photoluminescence. The ratio of observed nanotube densities therefore gives the semiconducting fraction in the sample. The method can be performed on SWNTs prepared by a variety of growth and/or post-processing methods. The results provide compositional reference data that is useful to researchers working with such samples or attempting to calibrate bulk analysis techniques.

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

EXEMPLARY ASPECTS

Example 1

Preparation of the Supported Catalysts

Catalysts were prepared by impregnating support materials in metal salt solutions. Three different groups of catalyst particles were synthesized and used for growing SWNTs by CVD. Narrow dispersed iron catalysts, with average diameters of about 5 nm and about 9 nm, were obtained by thermal decomposition of iron acetate in glycol solution under nitrogen atmosphere. $FeAc_2$ in methanol was used at a molar ratio of $Fe:Al_2O_3$ of 1:15. Under a nitrogen atmosphere, $FeAc_2$ was added to dietheylene glycol mono-n-butyl ether in the molar ratio of 1 mM:20 mM. The reaction mixture was mixed under the nitrogen atmosphere using a magnetic stir bar, and heated under reflux for 90 minutes. The reaction mixture was then cooled to room temperature, and $Al_2O_3$ (15 mM) was added at once. The reaction solution was stirred at room temperature for 15 minutes, and then heated to 150° C. for 3 hours. The reaction was cooled to 90° C. while flowing a stream of $N_2$ over the mixture to remove the solvent. A black film formed on the walls of the reaction flask. The black film was collected and ground with an agate mortar to obtain a fine black powder.

Example 2

Synthesis of Carbon Nanotubes

Carbon nanotubes were synthesized by using the experimental setup described in Harutyunyan et al., NanoLetters 2, 525 (2002). CVD growth of SWNTs, with the catalyst of Example 1, and methane as a carbon source (T=800° C., methane gas flow rate 60 sccm).

Example 3

SWNT Sample Preparation

Figure 2:
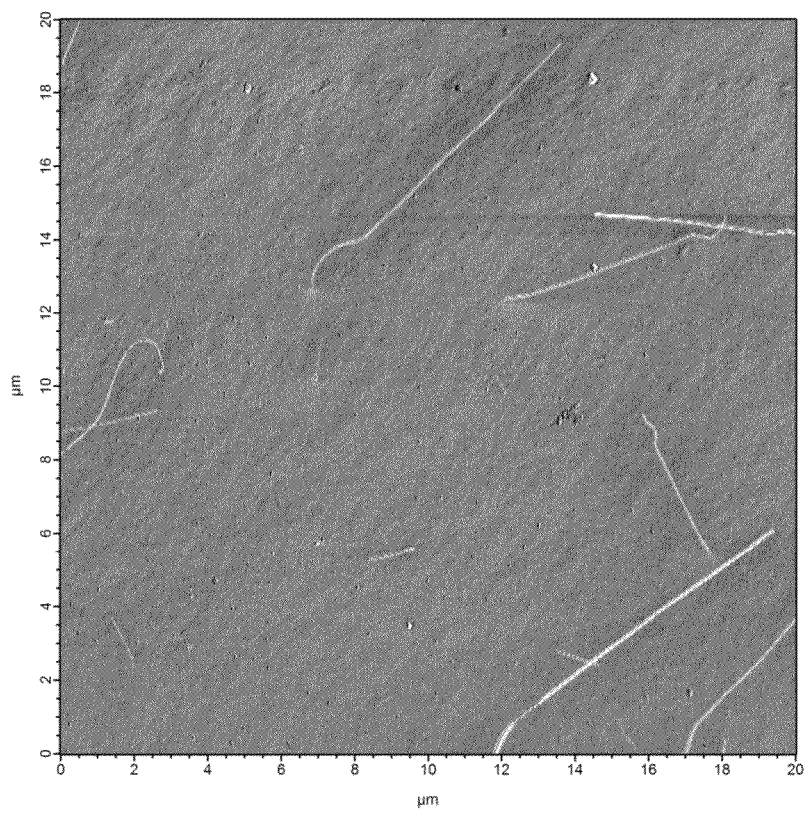
FIG. 2 depicts AFM images of individual SWNTs and is an example of an image type that can be used to determine the total numbers of SWNTs.

This example provides details regarding the preparation of several SWNT batches having been synthesized by various methods. These include raw product made by the HiPco method at Rice University (batch 166.12), by a CVD process at the Honda Research Institute USA Inc. (Columbus, Ohio), by laser ablation at NASA-Johnson Space Center, and by the University of Oklahoma CoMoCAT method at SouthWest Nanotechnologies Inc. The CoMoCAT sample was purified and freeze-dried before analysis. SWNTs that had been processed by density gradient separation at Northwestern University starting from raw HiPco SWNTs (Carbon Nanotechnologies, Inc., batch R0559) were also analyzed. Judging by the diameter distributions deduced from AFM image analysis (see FIG. 2), the photoluminescence emission of each of these SWNT samples was predicted to fall within the spectral range of the InGaAs detector used in these studies. Raw SWNT samples were initially bath sonicated for 3 hours in 1% aqueous sodium dodecyl sulfate (SDS) solutions to give concentrated SWNT suspensions. The suspensions were then centrifuged at 26700×g for 6 hours. To avoid excessive losses, the smaller CVD and laser ablation samples were instead centrifuged at 14500×g for 10 to 30 min in a table-top centrifuge. After centrifuging, the pellets were discarded and the supernatants were diluted by factors of 14-24 to adjust SWNT and SDS concentrations to convenient levels. These diluted suspensions were then tip-sonicated for 2 min at 5-7 W to disaggregate residual SWNT bundles before spin-coating onto polished fused silica slides. These slides had previously been spin coated with 0.05% aqueous SDS solution, rinsed with deionized water, and annealed for 30 min in air at 550° C. to obtain clean and flat surfaces.

A separate sample preparation procedure was used for density gradient sorted SWNTs. Those SWNTs were extracted from the density gradient in solutions containing SDS, sodium cholate, and iodixanol (Green et al., Nano Lett, 8:1417-1422 (2008)) and concentrated in step density gradients. To prevent uneven AFM backgrounds arising from sodium cholate and iodixanol aggregates, the samples were dialyzed against 1% w/v SDS aqueous solution for 49 hours using 20 k molecular-weight cutoff dialysis cassettes (Pierce Chemical), which removed the sodium cholate and iodixanol from solution. The dialyzed solutions were diluted by factors of 14-24 and subjected to intense bath sonication (Sharpertek ultrasonic cleaner). The resulting suspensions were then tip-sonicated for 30 seconds at 5 W and spin-coated onto 15×15× 0.15 mm mica slides.

Example 4

Quantitative Analysis of SWNTs

Figure 5:
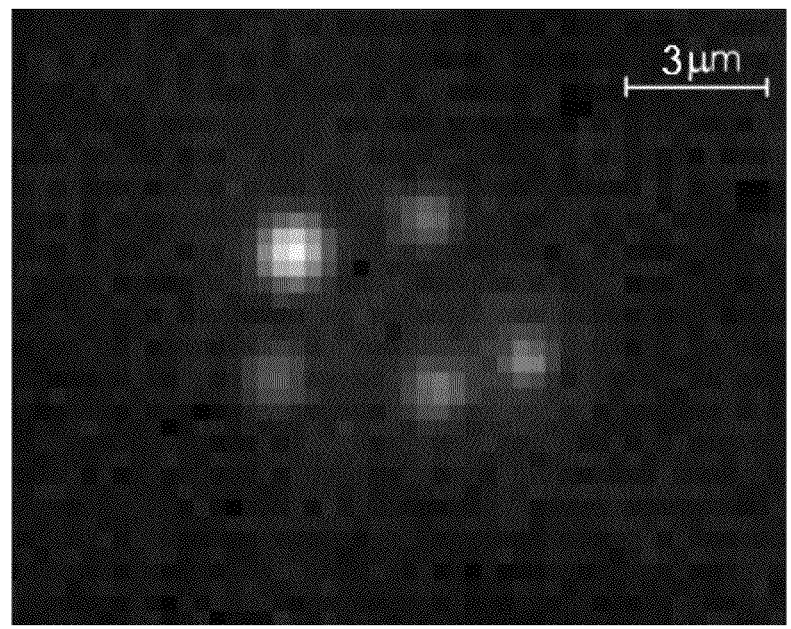
FIG. 5 depicts a near-IR photoluminescence image of individual SWNTs from the same DGU-processed semiconducting enriched sample in dried SDS on a cleaved mica surface as shown in FIG. 1.
Figure 6:
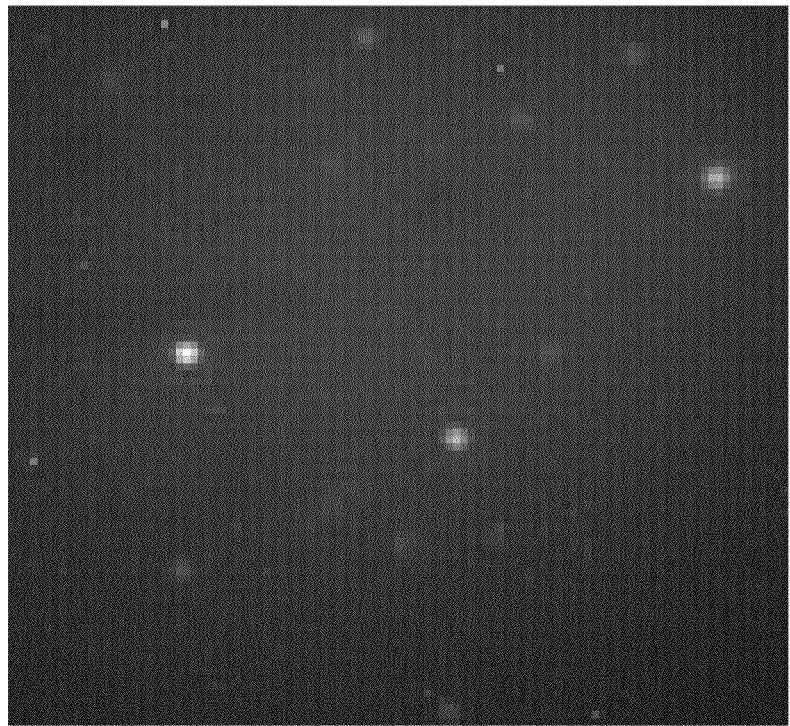
FIG. 6 depicts a photoluminescence image of individual SWNTs and is an example of an image that can be used to quantitate the numbers of semiconducting SWNTs.

Several SWNT batches produced by different methods are analyzed in this example. After the slides were coated with aqueous surfactant suspensions of SWNTs as described above in EXAMPLE 3, the total number of SWNTs per unit area was determined from atomic force microscopy (AFM) images, and the number of semiconducting SWNTs per unit area was found from near-IR photoluminescence images. A Veeco AFM (Multi-mode 3A) was used to study up to 40 regions, each 10×10 μm or 6×6 μm, within a ~100×100 μm area of the sample. The number of SWNTs in each image was counted using AFM (FIG. 1). Photoluminescence of individual semiconducting SWNTs in the sample was observed using a custom-built near-IR fluorescence microscope (Tsyboulski et al., Nano Lett, 5:975-979 (2005)). In this setup, semiconducting SWNTs were excited in their $E_{22}$ transitions with 660 and 780 nm diode lasers. This combination of excitation wavelengths induces detectable emission from essentially all semiconducting (n,m) species in the studied samples. This occurs because of the high detection sensitivity and the large effective resonance windows arising from long Lorentzian tails of the principal $E_{22}$ peaks, plus many weaker spectral features from $E_{22}$ vibronic sidebands, $E_{11}$ vibronic sidebands, higher excitonic bands associated with $E_{22}$, and underlying continuum-like transitions. Near-IR $E_{11}$ photoluminescence emission was collected through the quartz substrate by a Nikon Plan Apo 60×, NA=1 water immersion objective on a Nikon TE-2000U inverted microscope. Fluorescence of SWNTs on mica substrates was instead collected directly with a Nikon CF Plan 100×, NA=0.95 air objective. The microscope was coupled through a 946 nm long-pass filter to a liquid nitrogen-cooled Roper OMA V 2D InGaAs camera to image NIR emission from semiconducting SWNTs on the sample surface (FIG. 5). To monitor emission spectra of individual SWNTs, the emitted light from a small region of the image plane could be directed into a spectrograph and detected by a 512-channel InGaAs linear array. For each sample, numerous regions of 10×10 μm or 6×6 μm (depending on the magnification of the objective) were examined to find the number of semiconducting SWNTs per unit area. The semiconducting fraction in each sample was subsequently determined as the average of the ratio of the number of semiconducting SWNTs per unit area to the total number of SWNTs per unit area.

In these experiments, only individual, disaggregated SWNTs were counted. During AFM imaging, the few residual bundles were identified on the basis of height profiling and omitted from the counts (see FIG. 1, left panel, for height criteria). As seen from FIG. 1, the number of SWNTs per 6×6 μm region could be easily determined and their diameters estimated from height profile analysis. Individual SWNTs commonly showed height variations along their lengths attributed to regions of irregular surfactant coating. The minimum profile heights for SWNTs in FIG. 1 ranged from 0.7 to 1.35 nm. These values are consistent with the diameter distribution of SWNTs in these samples and are smaller than would be expected for bundled nanotubes.

Figure 4:
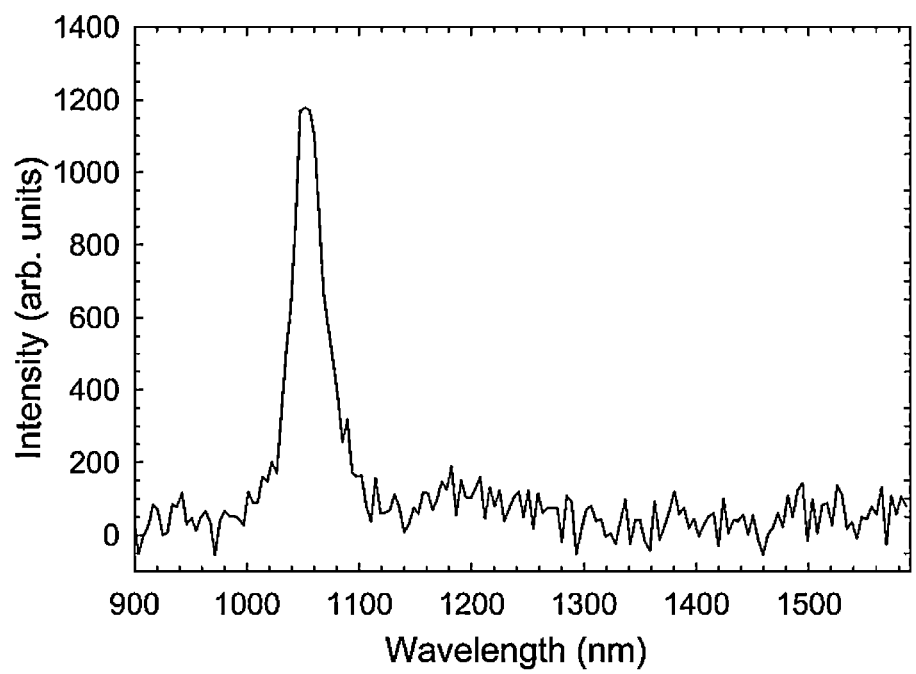
FIG. 4 depicts the near-IR photoluminescence spectrum of a single SWNT in dried SDS on a fused silica substrate.

To avoid counting loose aggregates, the emission spectra of objects that appeared not to be point emitters were examined and excluded if their spectra were broader or more complex than expected for an individual SWNT (see FIG. 4 for a normal emission spectrum). Bundles in samples containing significant metallic content are likely to be non-emissive, and therefore uncounted, because of efficient energy transfer to a metallic tube (O'Connell et al., Science, 297:593-596 (2002)). The fraction of nanotube objects appearing to be bundles in AFM images ranged from 5 to 15% (see FIG. 2) with semiconducting-rich samples falling near the bottom of this range and thus presenting only a minor chance for semiconducting bundle miscounting. Increased excitation intensities and integration times enable the discernment of weak emitters (e.g., unbundled semiconducing SWNTs having defects or surface functionalization) from background noise. In this way, it is possible to count imperfect SWNTs unless they were so damaged as to contain no electronically intact segments longer than ~100 nm. Under the processing conditions described herein, however, it is expected that only a negligible fraction of nanotubes sustained such extensive damage. SWNTs that are ultrasonically cut to lengths below 100 nm might also escape PL detection, but AFM data show that the vast majority of SWNTs in the present samples have lengths between 200 and 700 nm.

The present quantitative methods can involve a statistical sampling from multiple regions of the sample using AFM and photoluminescence. By obtaining AFM and PL counts from many distinct but nonregistered small regions and then adding the counts, a ratio can be determined that approaches the true ratio of semiconducting to metallic SWNTs over the entire sample. Each sample batch according to this example was examined typically at at least 40 different regions, each region being 10×10 μm or 6×6 μm, to give nanotube counts exceeding 200 for each method. The combined number of SWNTs counted in this study exceeds 12,000. Measurements for each sample batch were performed on three or more spin-coated replicates. Table 1 shows the semiconducting percentages computed by averaging these replicate determinations and the standard errors of the mean percentages. Measurement uncertainties are estimated to range from about 0.5% to about 4%.

TABLE 1

Compositions Determined for As-Produced or Processed SWNT Samples

| Sample | Source | % semiconducting | % metallic | % standard error |
| --- | --- | --- | --- | --- |
| HiPco | Rice Univ. | 62.9 | 37.1 | 0.5 |
| CoMoCAT, standard grade | SWeNT Inc. | 92.1 | 7.9 | 1.1 |
| CoMoCAT, commercial grade | SWeNT Inc. | 51.9 | 48.1 | 3.5 |
| laser ablation, low temperature method | ERC Inc./NASA-JSC | 54.7 | 45.3 | 1.4 |
| CVD preferential growth | Honda Res. Inst. USA Inc. | 15.4 | 84.6 | 2.6 |
| HiPco, starting material | Northwestern Univ. | 60.5 | 39.5 | 3.8 |
| HiPco, semiconducting-enriched by DGU | Northwestern Univ. | 96.0 | 4.0 | 0.6 |
| HiPco, metallic-enriched by DGU | Northwestern Univ. | 3.1 | 96.9 | 0.6 |

The results in Table 1 are consistent with expectations based on the growth and processing methods used to prepare the samples. For example, HiPco SWNTs are known to grow in a wide variety of (n,m) structures and are presumed to comprise a nearly statistical distribution of two-thirds semiconducting and one-third metallic nanotubes. The results in Table 1 show a HiPco semiconducting content within 4% of that expected value. The standard grade CoMoCAT SWNTs produced by a lower temperature process are known to contain high concentrations of the semiconducting (6,5) and (7,6) species (Bachilo et al., J Am Chem Soc, 125:11186-11187 (2003)) and can have a metallic content below the 33% statistical value. These findings confirm a high semiconducting fraction of 92.1% in a standard grade CoMoCAT sample.

It has been proposed that for small diameter nanotubes the formation of caps leading to zigzag nanotubes is thermodynamically and kinetically unfavorable (Gomez-Gualdron et al., Nanotechnology, 19:485604(1-7) (2008)). Likewise, it is believed that the preference for semiconducting near-armchair structures in CoMoCAT samples arises from a combination of the stability of the nanotube cap on a catalyst surface and the activation energy for carbon atom incorporation into the nanotube during growth. The caps for armchair nanotubes are stable, but for that reason also give higher activation energies for carbon incorporation and therefore decreased production of these metallic armchair species at low temperatures. By comparison, the growth interfaces of near-armchair species (e.g., (6,5), (7,6), etc.) are somewhat less stable and allow carbon incorporation with a lower activation energy. These differences among activation energies are expected to be greatest in the small-diameter region, narrowing the distribution of chiralities in samples synthesized at low temperatures compared to those synthesized at high temperatures (Lolli et al., J Phys Chem B, 110:2108-2115 (2006)). Accordingly, the commercial grade CoMoCAT sample, produced at higher temperatures, includes a broader range of species and is found here to contain only 52% semiconducting SWNTs.

It is also possible to tune a CVD growth process for even higher metallic contents. This is illustrated by samples from Honda Research Institute USA Inc., which were grown via methane decomposition on Fe nanocatalysts that were previously annealed in situ under inert gas ambient in the presence of oxidative species. This product is found to contain 15% semiconducting, and therefore 85% metallic SWNTs. This is the lowest semiconducting fraction found among the samples described herein that had not undergone post-growth separation treatments. It is also far lower than the semiconducting fractions found in the other CVD samples analyzed here. This analysis is consistent with an independent estimate of the semiconducting content obtained by analyzing ratios of integrated Raman radial breathing mode intensities (with 632.8 nm excitation) and comparing to a HiPco standard (Krupke et al., Science, 301:344-347 (2003)).

In addition to HiPco and CVD grown SWNTs, laser ablation samples grown at the NASA-Johnson Space Center (Arepalli et al., J Nanosci Nanotechnol, 4:762-773 (2004); Arepalli et al., Chem Phys Lett, 302:193 (1999); Arepalli et al., Appl Phys A, 70:125 (2000); Arepalli, J Nanosci Nanotechnol, 4:317 (2004)) were also analyzed. These SWNTs were produced at 900° C. in order to reduce the average diameter and bring $E_{11}$ transitions into the detection range of the spectrometer (Nikolaev et al., J Nanosci Nanotechnol, 10:3780-3789 (2010)). In this laser ablation sample, it was determined that there were 55% semiconducting nanotubes.

In order to further test the present methods and to characterize the semiconducting fraction in SWNT samples processed by density gradient ultracentrifugation (DGU) samples prepared at Northwestern University. These consisted of fractionated HiPco nanotubes enriched in semiconducting or metallic species. The semiconducting content of the starting material as well as of the enriched samples was determined. The starting material was found to have a semiconducting content within 2.5% of the value determined separately for HiPco SWNTs (see Table 1). However, the metallic and semiconducting enriched samples differed dramatically from the starting material, with semiconducting fractions of 2.6 and 96%, respectively (see Table 1). These results confirm highly selective electronic type sorting through the DGU processing and are consistent with purity estimates based on optical absorbance data (Green et al., Nano Lett, 8:1417-1422 (2008)).

While the invention has been particularly shown and described with reference to a preferred embodiment and various alternate embodiments, it will be understood by persons skilled in the relevant art that various changes in form and details can be made therein without departing from the spirit and scope of the invention. All printed patents and publications referred to in this application are hereby incorporated herein in their entirety by this reference.

What is claimed:

1. A method for quantitatively determining the ratio of metallic and semiconductor single-wall carbon nanotubes (SWNT) in a sample, the method comprising:
   debundling the SWNTs to provide substantially individual SWNTs;
   measuring an atomic force microscopy (AFM) signal from a sample, wherein the AFM signal is produced by SWNTs, and wherein SWNTs comprise a mixture of semiconductor and metallic SWNTs;
   measuring a photoluminescence (PL) signal from a sample, wherein the PL signal is produced by semiconductor SWNTs; and
   determining the ratio of metallic and semiconductor SWNTs in the sample by comparing the signals corresponding to the total SWNTs and semiconducting SWNTs,
   wherein the ratio of metallic and semiconductor SWNTs is quantitatively determined.

2. The method of claim 1, further comprising obtaining a count of the total SWNTs in the sample from the AFM signal and obtaining a count of the semiconductor SWNTs in the sample from the PL signal.

3. The method of claim 2, further comprising obtaining a count of the metallic SWNTs in the sample by subtracting the count of the semiconductor SWNTs from the count of the total SWNTs in the sample.

4. The method of claim 1, further comprising obtaining multiple measurements of the AFM signal and multiple measurements of the PL signal at various positions of the sample and further comprising combining the multiple measurements to obtain a total AFM signal and a total PL signal.

5. The method of claim 4, further comprising obtaining an average ratio of metallic and semiconductor SWNTs in the sample by comparing the total AFM signal and the total PL signal.

6. The method of claim 4, wherein each measurement of the AFM signal has a corresponding measurement of the PL signal at the same positions on the sample.

7. The method of claim 1, wherein debundling comprises sonication.

8. The method of claim 1, further comprising coating the individual SWNTs with a polymer to provide coated SWNTs.

9. The method of claim 1, further comprising depositing the SWNTs on a substrate.

10. The method of claim 8, wherein the polymer sulfonated polystyrene-block-poly(ethylene-ran-butylene)-block-polystyrene (SDPS), polyvinyl pyrrolidone (PVP), polystyrene sulfonate (PSS), polyvinyl sulfate, poly(sodium styrene sulfonic acid-co-maleic acid), dextran sulfate, or mixtures thereof.

11. The method of claim 10, wherein the polymer is SDPS.

12. The method of claim 9, wherein the substrate is quartz.

13. The method of claim 1 wherein the PL signal comprises near-infrared photoluminescence.

14. The method of claim 13 wherein the near-infrared photoluminescence comprises near-infrared fluorescence.

* * * * *